United States Patent
Richards (10) Patent No.: US 7,708,783 B2
(45) Date of Patent: May 4, 2010

(54) ROTATING CONSTRAINED LINER

(75) Inventor: Mark I Richards, Leander, TX (US)

(73) Assignee: Zimmer Technology, Inc., Warsaw, IN (US)

( * ) Notice: Subject to any disclaimer, the term of this patent is extended or adjusted under 35 U.S.C. 154(b) by 143 days.

(21) Appl. No.: 11/267,796

(22) Filed: Nov. 4, 2005

(65) Prior Publication Data

US 2007/0106390 A1   May 10, 2007

(51) Int. Cl.
*A61F 2/32* (2006.01)
(52) U.S. Cl. .................................. 623/22.15
(58) Field of Classification Search ... 623/19.11–19.14, 623/22.11–23.38
See application file for complete search history.

(56) References Cited

U.S. PATENT DOCUMENTS

| | | | |
|---|---|---|---|
| 2,900,292 A | | 8/1959 | Coleman, Jr. et al. |
| 3,683,421 A | * | 8/1972 | Martinie .................. 623/22.13 |
| 3,903,549 A | * | 9/1975 | Deyerle ................... 623/22.36 |
| 3,978,528 A | * | 9/1976 | Crep ....................... 623/19.12 |
| 4,642,123 A | * | 2/1987 | Noiles ....................... 623/22.2 |
| 4,678,472 A | | 7/1987 | Noiles |
| 4,770,658 A | * | 9/1988 | Geremakis ............... 623/22.19 |
| 4,813,963 A | | 3/1989 | Hori et al. |
| 5,092,897 A | * | 3/1992 | Forte ....................... 623/22.18 |
| 5,282,864 A | | 2/1994 | Noiles et al. |
| 5,310,408 A | * | 5/1994 | Schryver et al. ......... 623/22.37 |
| 5,314,487 A | * | 5/1994 | Schryver et al. ......... 623/22.37 |
| 5,314,491 A | * | 5/1994 | Thongpreda et al. ..... 623/22.29 |
| 5,362,311 A | | 11/1994 | Amino et al. |
| 5,383,938 A | * | 1/1995 | Rohr et al. ............... 623/22.29 |
| 5,507,824 A | * | 4/1996 | Lennox .................... 623/22.25 |
| 5,549,691 A | * | 8/1996 | Harwin .................... 623/22.37 |
| 5,549,701 A | * | 8/1996 | Mikhail ................... 623/22.21 |
| 5,593,445 A | | 1/1997 | Waits |

(Continued)

FOREIGN PATENT DOCUMENTS

EP   0086879 A1   8/1983

(Continued)

OTHER PUBLICATIONS

Webpage—Zimmer Product—Epsilon Durasul Constrained Insert, 4 pages, 2005 Zimmer, Inc.

(Continued)

*Primary Examiner*—David J Isabella
*Assistant Examiner*—Ann Schillinger
(74) *Attorney, Agent, or Firm*—Baker & Daniels LLP (57) ABSTRACT

An acetabular component for a prosthetic hip joint generally consists of an acetabular shell and an acetabular liner. The acetabular liner includes a cup portion and at least one constraining portion. The cup portion has a hemispherical or dome-shape that defines a hemispherical cavity for receiving a femoral head of a femoral component. The constraining portions may include extensions for retaining the femoral head in the cavity of the cup portion. The liner further includes cutout portions between the constraining portions. The acetabular liner is rotatable within the acetabular shell to provide a complete range of motion to the femoral component without fear of impingement, subluxation, or dislocation of the femoral head. The constraining portions may include inclined surfaces to induce rotation of the acetabular liner within the acetabular shell.

20 Claims, 5 Drawing Sheets

U.S. PATENT DOCUMENTS

| | | | |
|---|---|---|---|
| 5,725,591 A * | 3/1998 | DeCarlo et al. | 623/22.29 |
| 5,725,597 A * | 3/1998 | Hwang | 623/22.15 |
| 5,824,108 A * | 10/1998 | Huebner | 623/22.29 |
| 5,938,698 A | 8/1999 | Sandoz et al. | |
| 5,989,294 A * | 11/1999 | Marlow | 623/22.16 |
| 6,231,612 B1 | 5/2001 | Balay et al. | |
| 6,328,764 B1 | 12/2001 | Mady | |
| 6,475,243 B1 | 11/2002 | Sheldon et al. | |
| 6,527,808 B1 * | 3/2003 | Albertorio et al. | 623/22.26 |
| 6,589,284 B1 | 7/2003 | Silberer | |
| 6,610,097 B2 | 8/2003 | Serbousek et al. | |
| 6,620,200 B1 | 9/2003 | Descamps et al. | |
| 6,736,852 B2 * | 5/2004 | Callaway et al. | 623/19.14 |
| 6,827,742 B2 | 12/2004 | Hayes et al. | |
| 6,916,342 B2 * | 7/2005 | Frederick et al. | 623/22.29 |
| 6,976,999 B2 | 12/2005 | Charlebois et al. | |
| 7,115,145 B2 * | 10/2006 | Richards | 623/22.29 |
| 7,208,222 B2 | 4/2007 | Rolfe et al. | |
| 2001/0037156 A1 | 11/2001 | Burstein et al. | |
| 2003/0050703 A1 * | 3/2003 | Harris et al. | 623/22.2 |
| 2003/0105529 A1 * | 6/2003 | Synder et al. | 623/22.24 |
| 2003/0187512 A1 * | 10/2003 | Frederick et al. | 623/22.2 |
| 2005/0004677 A1 * | 1/2005 | Johnson | 623/22.19 |
| 2005/0004678 A1 | 1/2005 | Richards | |
| 2005/0102034 A1 * | 5/2005 | Hayes et al. | 623/22.28 |
| 2005/0240276 A1 | 10/2005 | Shea et al. | |
| 2006/0226570 A1 | 10/2006 | Case | |
| 2006/0241781 A1 * | 10/2006 | Brown et al. | 623/23.43 |
| 2007/0239283 A1 | 10/2007 | Newsome et al. | |

FOREIGN PATENT DOCUMENTS

| | | |
|---|---|---|
| EP | 0694294 A1 | 1/1996 |
| EP | 0773007 A1 | 5/1997 |
| FR | 2357235 | 2/1978 |
| FR | 2684544 A1 | 6/1993 |
| FR | 2824258 A1 | 11/2000 |
| FR | 2805151 A1 | 8/2001 |
| GB | 2306330 A | 1/2008 |
| WO | WO00/64383 A1 | 11/2000 |

OTHER PUBLICATIONS

The International Search Report issued in related International Application No. PCT/US2006/060504 on Jan. 28, 2008.

Wright Medical Technology, Inc., "Lineage Acetabular Cup System Surgical Technique," copyright 2003, Arlington, TN 38002 (12 pages).

Office Action mailed Jun. 18, 2007, in U.S. Appl. No. 11/104,351.

* cited by examiner

FIG_1

FIG_2

FIG_3

FIG_4

FIG_7

FIG_8B

ROTATING CONSTRAINED LINER

BACKGROUND

1. Field of the Invention

The present invention relates to a constrained liner for a prosthetic hip joint, and, more particularly, to a rotating constrained liner for a prosthetic hip joint.

2. Description of the Prior Art

Acetabular prostheses generally consist of two separate components, an acetabular shell and an acetabular liner. The shell has a hemispherical shape and is affixed and embedded into a cavity formed in a natural acetabulum of a patient. The liner has a hemispherical shape to mate with an internal cavity of the shell. A low-friction bearing surface is formed along a spherical cavity in the liner and provides an articulation surface for a femoral ball of a hip stem.

The shell may be made of a biocompatible metal or metal alloy, and the liner may be made of a polymer, such as ultra-high molecular weight polyethylene (UHMWPE). Regardless of the materials or geometries, these two components are generally locked together with the liner fitted within the shell and the shell encompassing the external surface of the liner. Once the shell is embedded in bone of the natural acetabulum and the liner has been assembled within the shell, the liner is ready to receive the femoral ball.

Hip prostheses can potentially experience impingement, subluxation, and even dislocation after being implanted in the patient. For instance, the spherical femoral ball of the hip stem can become dislocated from the acetabular component. This dislocation can occur from various reasons, such as trauma to the leg or abnormal twisting of the leg. In some instances, an additional surgical procedure is required to remedy dislocation of a prosthetic hip.

Due to the potential occurrence of impingement and subluxation, it is desirable to have an acetabular liner that inhibits subluxation and dislocation of the femoral ball from the acetabular component. In some designs, the liner is configured to have more than a hemispherical shape, i.e., the liner encloses and captures more than half of the femoral ball within the spherically shaped cavity of the liner. In some instances, a locking ring is used to lock the femoral ball into the cavity of the acetabular liner.

Conventional constrained liners, while providing additional stability to the prosthetic hip joint, inherently reduce the range of motion of the prosthetic hip joint because the femoral neck of the femoral component impinges on the extended portions of the constrained liner which extend beyond the hemispherical shape.

Solutions developed to increase the range of motion while still maintaining the advantages of constrained liners, i.e., reduction of impingement, subluxation, and dislocation, is to remove material, e.g., provide two cutouts, from the extended portion of the liner. The cutouts allow the femoral component to move through a range of motion similar to an unconstrained device, yet still maintain the advantages of having a constrained liner because the cutouts effectively leave two constraining portions extending from the liner. The range of motion is only restored to such a state, however, if the femoral component is moving within the cutout area. Therefore, the radial placement, i.e., "clocking," of the liner is important.

SUMMARY

The present invention provides a constrained liner for a prosthetic hip joint, and, more particularly, a rotating constrained liner for a prosthetic hip joint. In one embodiment, the rotating constrained liner is adapted to be rotationally connected to an acetabular shell to form an acetabular prosthesis which is inserted into a bone cavity of the natural acetabulum.

In one form thereof, the present invention provides a prosthetic joint assembly including a shell; a liner rotatably receivable within the shell and defining perpendicular longitudinal and hemispherical axes including a base portion substantially disposed on a first side of the hemispherical axis; and at least one constraining element projecting from the base portion and substantially disposed on a second side of the hemispherical axis, each constraining element including at least one inclined surface; and a prosthesis including a neck and a head, the head receivable within the liner, whereby contact between the neck and the at least one inclined surface induces rotational movement of the liner within the shell about the longitudinal axis.

In another form thereof, the present invention provides an acetabular cup for use with a prosthetic hip joint assembly including a femoral component having a femoral head and a femoral neck including an acetabular shell; and a liner rotatably receivable within the acetabular shell and defining perpendicular longitudinal and hemispherical axes including a base portion substantially disposed on a first side of the hemispherical axis; and at least one constraining element projecting from the base portion and substantially disposed on a second side of the hemispherical axis, each constraining element including at least one inclined surface.

In yet another form thereof, the present invention provides an acetabular cup for use with a prosthetic hip joint assembly including a femoral component having a femoral head and a femoral neck including an acetabular shell; and a liner rotatably receivable within the acetabular shell and defining perpendicular longitudinal and hemispherical axes including a base portion substantially disposed on a first side of the hemispherical axis; and means for constraining the femoral head within the liner, the means for constraining including means for inducing rotation of the liner within the acetabular shell about the longitudinal axis upon contact with the femoral neck.

In still another form thereof, the present invention provides a prosthetic joint assembly for receiving a prosthesis including a shell; and a liner rotatably receivable within the shell.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. Although the drawings represent embodiments of the present invention, the drawings are not necessarily to scale and certain features may be exaggerated in order to better illustrate and explain the present invention. The exemplifications set out herein illustrate embodiments of the invention, and such exemplifications are not to be construed as limiting the scope of the invention in any manner.

DETAILED DESCRIPTION

The embodiments disclosed below are not intended to be exhaustive or limit the invention to the precise forms disclosed in the following detailed description. Rather, the embodiments are chosen and described so that others skilled in the art may utilize their teachings.

Figure 1:
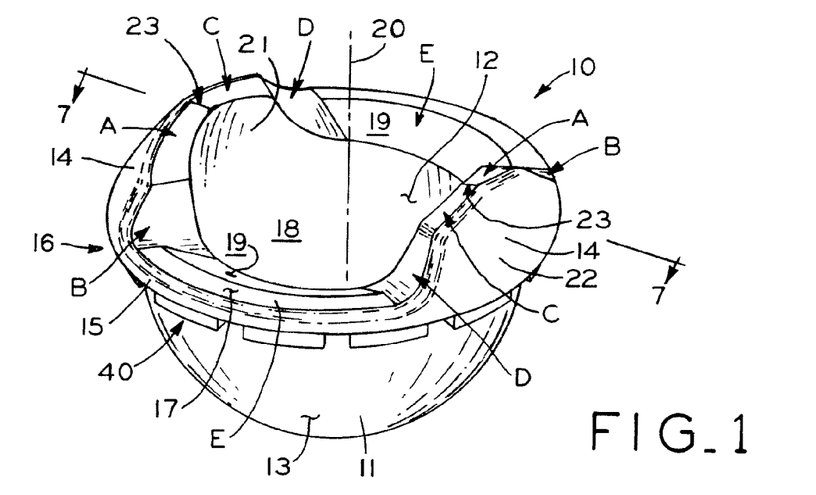
FIG. 1 is a perspective view of an exemplary rotating constrained liner of the present invention.
Figure 7:
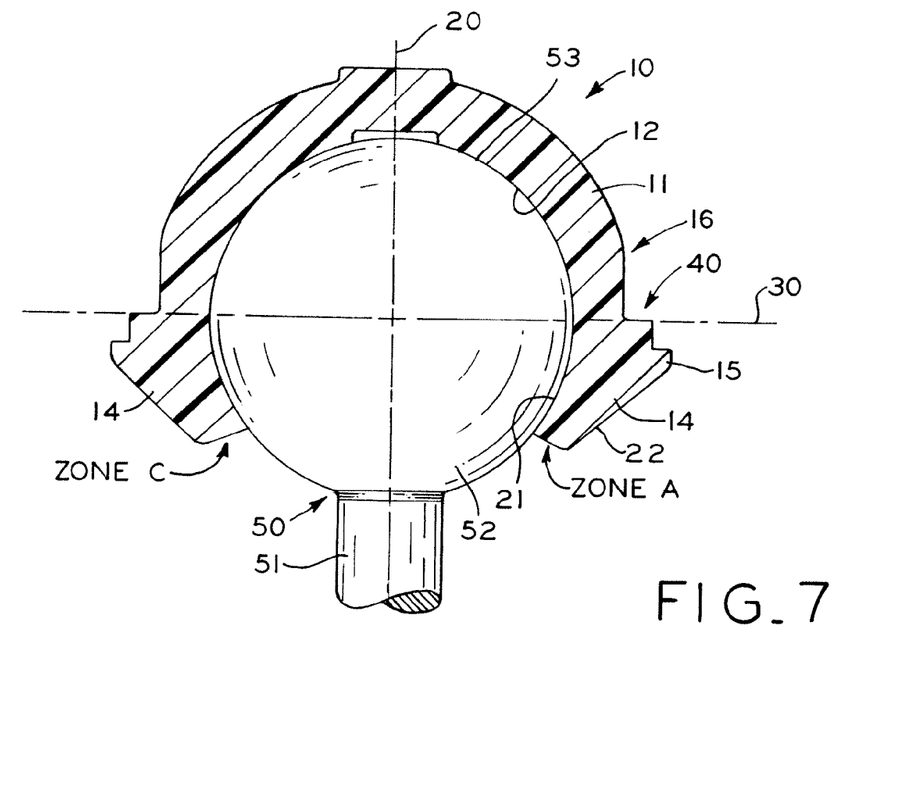
FIG. 7 is a cross-sectional view of the liner of FIG. 1, taken along line 7-7, further illustrating a femoral head secured within the liner via the constraining portions of the liner.
Figure 8A:
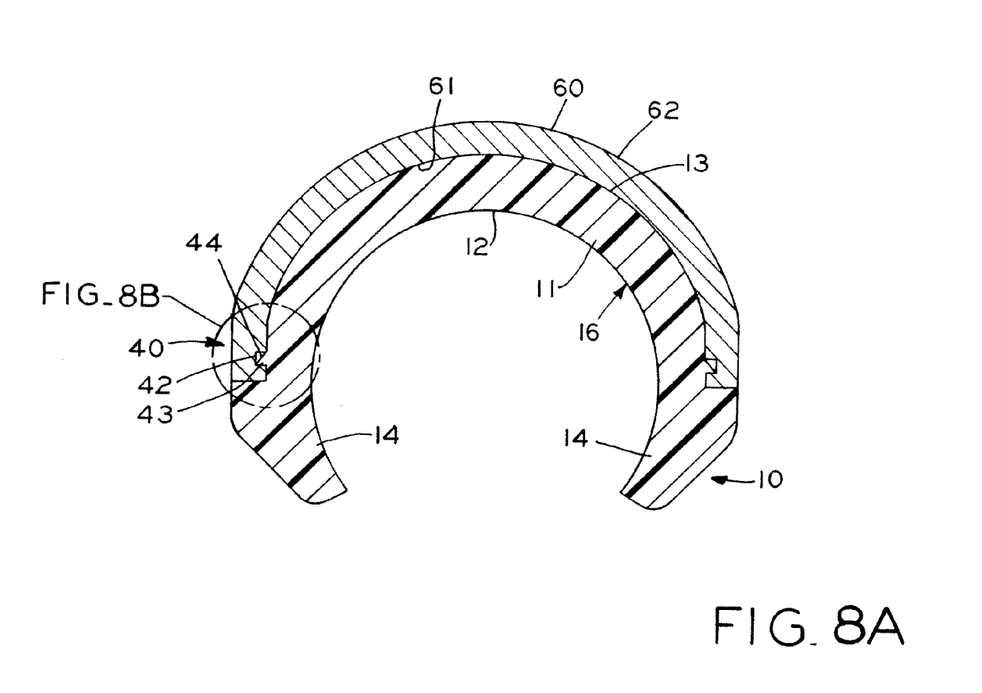
FIG. 8A is a cross-sectional view of an alternative liner, further illustrating the liner engaged with an acetabular shell.
Figure 9:
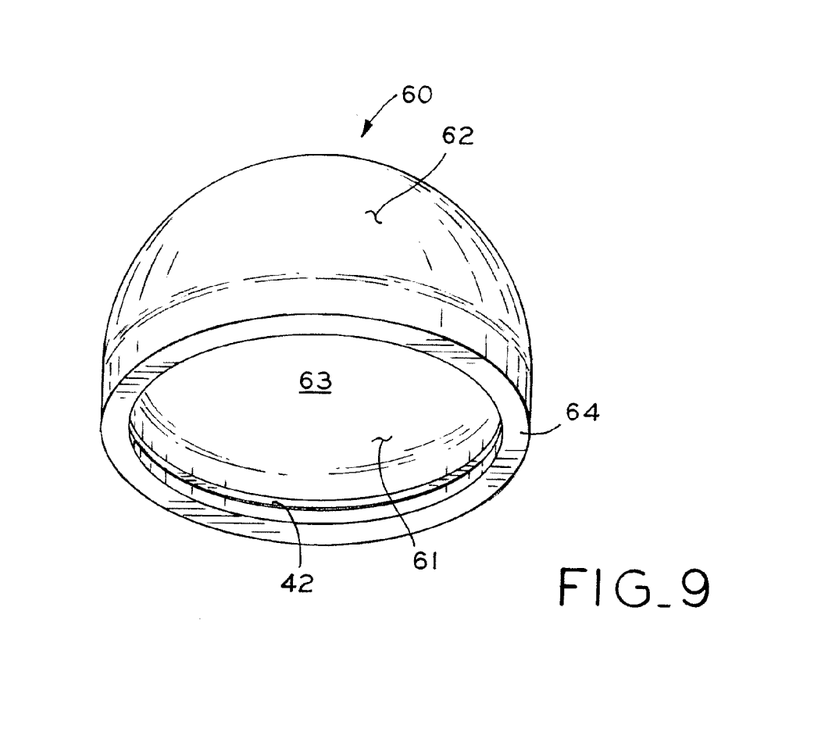
FIG. 9 is a perspective view of the acetabular shell of FIG. 8A.

Referring now to FIG. 1, an exemplary rotating constrained liner 10 is shown including cup portion 11 and a pair of constraining portions 14. As described below, liner 10 is received within acetabular shell 60 (FIG. 8A) of a prosthetic hip joint assembly which additionally includes a femoral prosthesis having a femoral head and a femoral neck. The femoral head of the femoral prosthesis is positioned within liner 10. Cup portion 11 generally has a partially spherical or dome-shaped body with outer surface 13 and inner surface 12. Inner surface 12 defines a partial spherical or hemispherical cavity 18 for receiving a femoral head or ball 52 (FIG. 7) of a femoral component 50 (FIG. 7). Inner surface 12 has a concave shape with a smooth articulating wall or surface adapted to articulate with femoral head 52. Outer surface 13 has a hemispherical or dome shape with a surface that is adapted to engage an inner surface 61 of an acetabular shell 60 (FIGS. 8A and 9). Annular rim 15 extends around an outer perimeter of cup portion 11 along base portion 16. Base portion 16 includes a distal end with annular platform or ring-shaped surface 17 that provides an entrance way or opening into cavity 18 of cup portion 11. Two extensions or constraining portions 14 extend outwardly from surface 17. Preferably, portions 14 are oppositely disposed from one another. Constraining portions 14 each may include Zones A, B, C, and D located on the edge of portion 14 that extends away from cup portion 11.

As shown in FIGS. 1 and 7, constraining portions 14 each include inner wall 21 and outer wall 22. Both walls 21 and 22 circumferentially extend around a circumferential perimeter of cup portion 11, i.e., around a portion of annular rim 15. Inner wall 21 may have a smooth surface with a spherical contour and may be arcuately directed toward central longitudinal axis 20. Similarly, outer wall 22 may have a smooth surface and may be arcuately directed toward central longitudinal axis 20.

Figure 2:
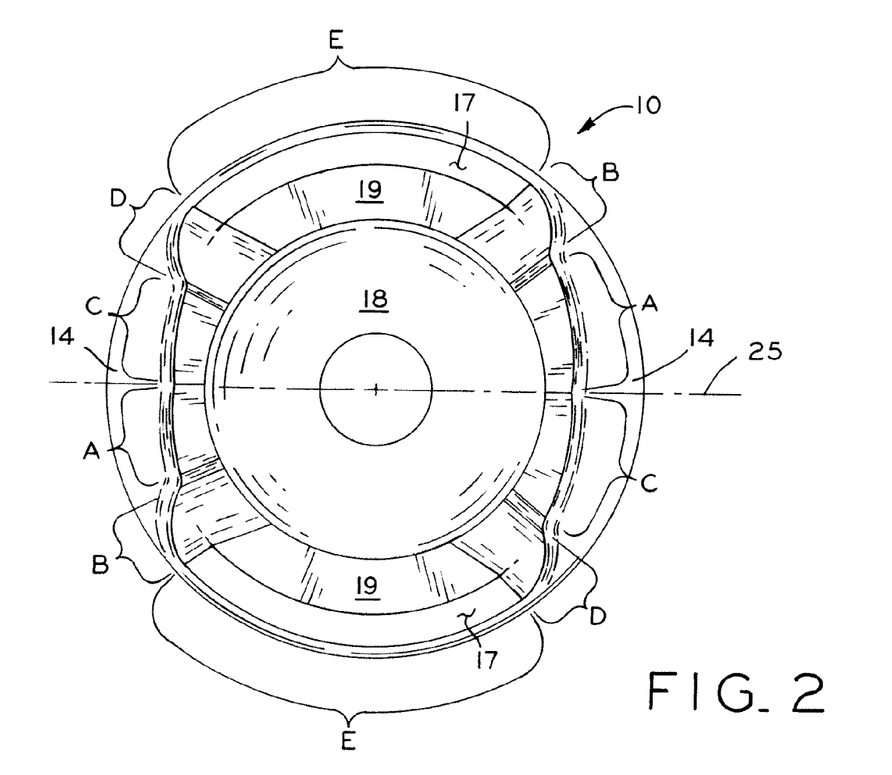
FIG. 2 is a bottom plan view of the liner of FIG. 1.

Referring now to FIGS. 1 and 2, outer wall 22 of each constraining portion 14 extends from Zone B, through Zones A and C, and ends with Zone D. Zones B and D are generally sloped towards Zone E on opposite sides of each constraining portion 14 and generally taper in width from Zone E to Zones A and C, respectively. Zones A and C are generally sloped towards Zones B and D, respectively, and generally slightly taper in width from Zones B and D, respectively, towards apex 23. In one embodiment, the slope in these zones is constant, gradual, and symmetric with respect to each other, i.e., Zones B and D have an identical slope and Zones A and C have an identical slope. In one embodiment, Zones B and D have a steeper incline or pitch than Zones A and C. In another embodiment, Zones A and C have a steeper incline or pitch than Zones B and D. Zones A, B, C, and D include angled or inclined faces to advantageously induce rotation of liner 10 about central longitudinal axis 20, as described below. Zones E are substantially flat and disposed around the circumference of annular rim 15 between constraining portions 14. When femoral neck 51 (FIG. 7) is positioned within Zone E, femoral neck 51 does not impinge on constraining portions 14.

In an exemplary embodiment, constraining portions 14 are opposed to one another, are similarly shaped, and have the same size. Alternatively, constraining portions 14 may be formed in different sizes, e.g., one constraining portion 14 may be larger than the other. In yet another alternative embodiment, constraining portions 14 are not similarly shaped, e.g., one constraining portion 14 may take the general shape as shown in FIG. 1 and another constraining portion 14 may take the general shape of a rectangle or triangle.

As shown in FIGS. 1 and 2, constraining portions 14 do not completely circumferentially extend around surface 17. Instead, two gaps or cutouts 19 are formed between constraining portions 14. Cutouts 19 are opposed to one another across central transverse axis 25.

Referring now to FIG. 7, cup portion 11 has a spherical configuration. Hemispherical axis 30 approximates the hemispherical line through cup portion 11. Base portion 16 of cup portion 11 may generally be disposed on a first side of hemispherical axis 30. Constraining portions 14 project from cup portion 11 and are disposed on a second side of hemispherical axis 30 to capture and retain femoral head 52 of femoral component 50. Inner walls 21 of constraining portions 14 form a partial spherical surface that provides a continuous spherical extension below surface 17 (FIG. 1) and below hemispherical axis 30.

Upon insertion of femoral head 52 in cavity 18 such that outer surface 53 of femoral head 52 can smoothly articulate with inner surface 12 of cup portion 11, constraining portions 14 radially flex outwardly away from central longitudinal axis 20 to accommodate passage of the diameter of femoral head 52 therebetween. Once femoral head 52 is positioned in cavity 18, constraining portions 14 resiliently flex back to their original position and capture femoral head 52 within cavity 18. As such, femoral head 52 is lockingly captured or retained within cavity 18 of cup portion 11.

Upon removal of femoral head 52 from cavity 18 of cup portion 11, constraining portions 14 radially flex outwardly away from central longitudinal axis 20 to accommodate passage of the diameter of femoral head 52 therebetween. Once femoral head 52 is removed, constraining portions 14 resiliently flex back to their original position.

Liner 10 may be made from different biocompatible materials, for example, highly cross-linked UHMWPE, titanium, cobalt chrome alloy, or stainless steel. In an exemplary embodiment, liner 10 is fabricated from a material which allows resilient flexibility of constraining portions 14 for snap-fitting femoral head 52 within cavity 18 in the manner described above. Liner 10 also includes shell/liner interface 40 which allows rotation of liner 10 relative to acetabular shell 60 about central longitudinal axis 20.

Figure 8B:
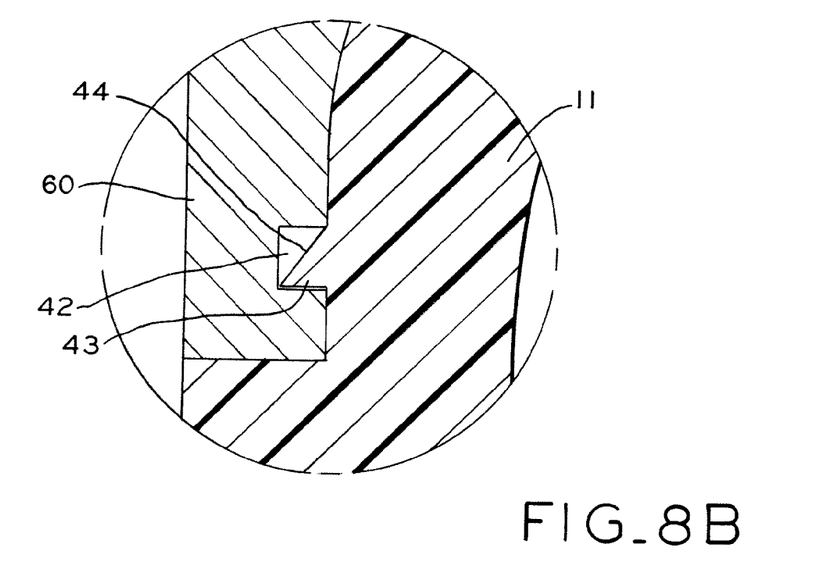
FIG. 8B is a close-up fragmentary view of a portion of the liner and shell of FIG. 8A.

As shown in FIGS. 8A and 8B, liner 10 includes an axial movement retention element, as described below. In one embodiment, the axial movement retention element is protrusion 43 which extends circumferentially around cup portion 11. Acetabular shell 60, as shown in FIGS. 8A, 8B, and 9, includes inner surface 61, outer surface 62, cavity 63, and circumferential edge 64. Groove 42 is positioned in inner surface 61 and near circumferential edge 64 of acetabular shell 60. As best shown in FIG. 8B, in one embodiment, protrusion 43 may include inclined face 44 to facilitate insertion of liner 10 into acetabular shell 60, as described below.

To insert liner 10 into acetabular shell 60, liner 10 is forced into cavity 63 of acetabular shell 60 with a force sufficient to slightly deform circumferential edge 64 radially outward such that edge 64 moves slightly away from liner 10. Liner 10 is forced into cavity 63 until protrusion 43 mates with groove 42 in acetabular shell 60. In an exemplary embodiment, inner surface 61 of acetabular shell 60 contacts outer surface 13 of cup portion 11 of liner 10 upon mating engagement of protrusion 43 with groove 42. In one embodiment, protrusion 43 includes inclined face 44 to facilitate the initial insertion of liner 10 into cavity 63 of acetabular shell 60. Inclined face 44 provides a gradual introduction of protrusion 43 into cavity 63 and eases the deformation process of forcing circumferential edge 64 radially outward. In an alternative embodiment, protrusion 43 may take any shape which facilitates insertion of liner 10 into cavity 63 of acetabular shell 60. The engagement of protrusion 43 in groove 42 allows rotation of liner 10 within acetabular shell 60 with respect to central longitudinal axis 20 while simultaneously preventing relative axial translation between acetabular shell 60 and liner 10 along central longitudinal axis 20.

To reduce the potential wear between liner 10 and acetabular shell 60, a crosslinked polyethylene bearing may be inserted into groove 42 or a metal-on-metal interface may be used. Alternatively, the axial movement retention element is a locking ring wherein groove 42 may continue to circumferential edge 64 and liner 10 may be inserted into acetabular shell 60 after which a locking ring may be inserted in groove 42 to both axially lock the liner and the acetabular shell and provide a bearing surface formed of crosslinked polyethylene or metal. In another alternative embodiment of the axial movement retention element, shell/liner interface 40 may employ a C-ring configuration to axially lock the liner and the acetabular shell, as fully described in U.S. Pat. No. 5,383,938, the disclosure of which is hereby expressly incorporated herein by reference.

In another alternative embodiment, shell/liner interface 40 may include a bayonet lock configuration (not shown) wherein the acetabular shell has a series of radially inwardly-directed protrusions and the liner has a series of cooperating radially outwardly-directed protrusions. The shell protrusions include cutouts between them to accommodate insertion of the liner into the acetabular shell. Once inside the internal cavity of the acetabular shell, the liner is rotated. Such rotation locks the liner to prevent axial displacement along central longitudinal axis 20. In an exemplary embodiment, the protrusions on the acetabular shell and the liner should be chosen to minimize the possibility of the protrusions on the liner lining up with the cutouts in the acetabular shell which would allow axial translation between the liner and the acetabular shell along central longitudinal axis 20.

Interface 40 may be constructed of any configuration which prevents axial translation of liner 10 and acetabular shell 60 along central longitudinal axis 20 while simultaneously allowing rotational translation of liner 10 and acetabular shell 60 about central longitudinal axis 20.

Figure 3:
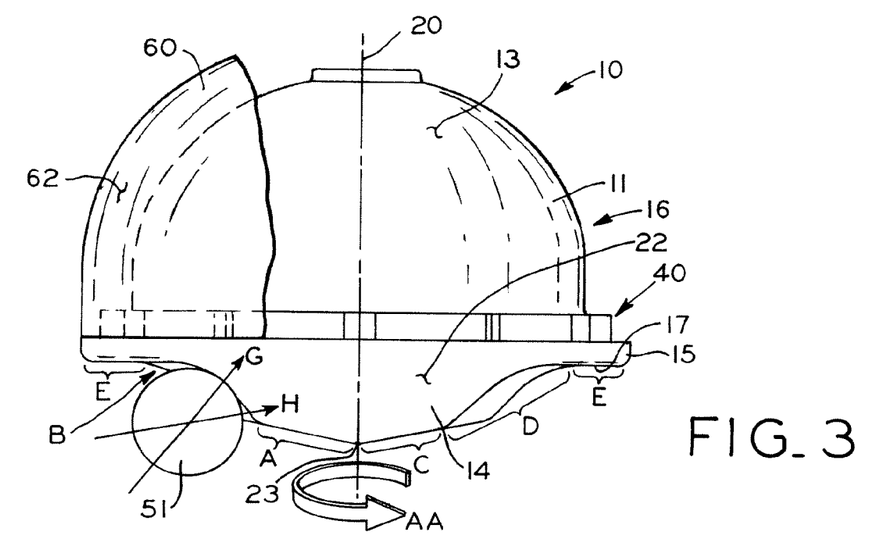
FIG. 3 is a side plan view of the liner of FIG. 1 and a fragmentary view of a portion of an acetabular shell, further illustrating impingement by a femoral neck on Zone B of the constraining portion of the liner.

In operation, as shown in FIG. 3, upon femoral neck 51 impinging on Zone B, i.e., femoral neck 51 moving in the general directions of Arrows G or H, a rotation of liner 10 with respect to acetabular shell 60 about central longitudinal axis 20 is induced in the general direction of Arrow AA to force femoral neck 51 to rest in Zone E. Rotation of liner 10 is induced by the inclined sloped surface formed in Zone B. As femoral neck 51 impinges on constraining portion 14 in Zone B, the inclined surface forces liner 10 to rotate in a clockwise direction (clockwise looking towards the bottom of liner 10) within acetabular shell 60 and move constraining portion 14 away from femoral neck 51 so that femoral neck 51 rests in Zone E where no impingement of femoral neck 51 on constraining portion 14 occurs.

Figure 4:
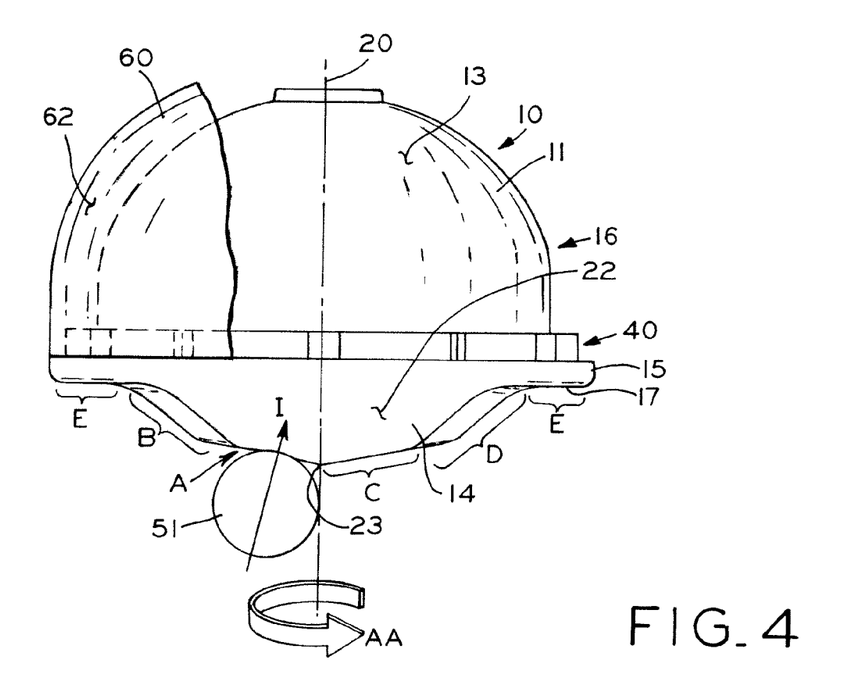
FIG. 4 is a side plan view of the liner of FIG. 1 and a fragmentary view of a portion of an acetabular shell, further illustrating impingement by a femoral neck on Zone A of the constraining portion of the liner.

Similarly, as shown in FIG. 4, upon femoral neck 51 impinging on Zone A, i.e., femoral neck 51 moving in the general direction of Arrow I, a rotation of liner 10 with respect to acetabular shell 60 about central longitudinal axis 20 is induced in the general direction of Arrow AA to force femoral neck 51 to rest in Zone E. Rotation of liner 10 is induced by the inclined sloped surface formed in Zone A. As femoral neck 51 impinges on constraining portion 14 in Zone A, the inclined surface forces liner 10 to rotate in a clockwise direction within acetabular shell 60 and move constraining portion 14 away from femoral neck 51 so that femoral neck 51 impinges on Zone B. Once femoral neck 51 impinges on Zone B, the action as described above with respect to FIG. 3 forces femoral neck 51 to rest in Zone E where no impingement of femoral neck 51 on constraining portion 14 occurs. Alternatively, the inclined surface in Zone A may be sufficient to force rotation of liner 10 to where femoral neck 51 rests in Zone E without intermediate impingement on Zone B.

Figure 5:
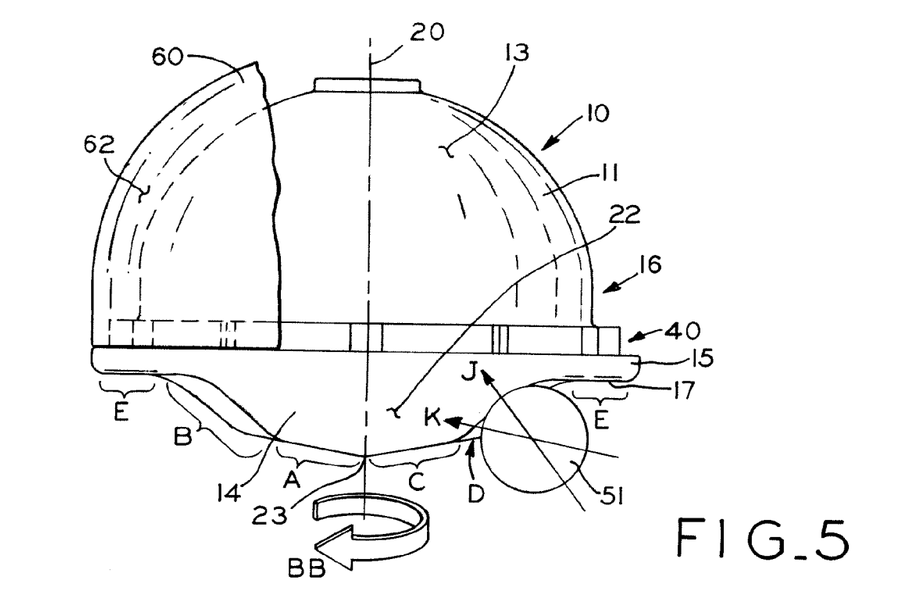
FIG. 5 is a side plan view of the liner of FIG. 1 and a fragmentary view of a portion of an acetabular shell, further illustrating impingement by a femoral neck on Zone D of the constraining portion of the liner.

As shown in FIG. 5, upon femoral neck 51 impinging on Zone D, i.e., femoral neck 51 moving in the general directions of Arrows J or K, a rotation of liner 10 with respect to acetabular shell 60 about central longitudinal axis 20 is induced in the general direction of Arrow BB to force femoral neck 51 to rest in Zone E. Rotation of liner 10 is induced by the inclined sloped surface formed in Zone D. As femoral neck 51 impinges on constraining portion 14 in Zone D, the inclined surface forces liner 10 to rotate in a counterclockwise direction within acetabular shell 60 and move constraining portion 14 away from femoral neck 51 so that femoral neck 51 rests in Zone E where no impingement of femoral neck 51 on constraining portion 14 occurs.

Figure 6:
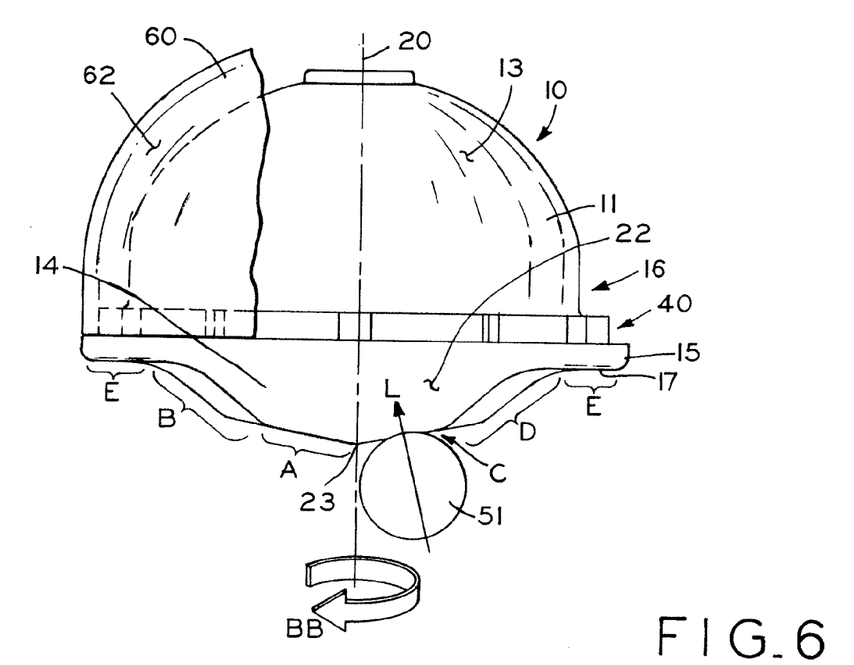
FIG. 6 is a side plan view of the liner of FIG. 1 and a fragmentary view of a portion of an acetabular shell, further illustrating impingement by a femoral neck on Zone C of the constraining portion of the liner.

Similarly, as shown in FIG. 6, upon femoral neck 51 impinging on Zone C, i.e., femoral neck 51 moving in the general direction of Arrow L, a rotation of liner 10 with respect to acetabular shell 60 about central longitudinal axis 20 is induced in the general direction of Arrow BB to force femoral neck 51 to rest in Zone E. Rotation of liner 10 is induced by the inclined sloped surface formed in Zone C. As femoral neck 51 impinges on constraining portion 14 in Zone C, the inclined surface forces liner 10 to rotate in a counterclockwise direction within acetabular shell 60 and move constraining portion 14 away from femoral neck 51 so that femoral neck impinges on Zone D. Once femoral neck 51 impinges on Zone D, the action as described above with respect to FIG. 5 forces femoral neck 51 to rest in Zone E where no impingement of femoral neck 51 on constraining portion 14 occurs. Alternatively, the inclined surface in Zone C may be sufficient to force rotation of liner 10 to where femoral neck 51 rests in Zone E without intermediate impingement on Zone D.

Impingement in Zones A and C, as described above, generally indicate an extreme configuration between shell 60 and femoral component 50. For example, impingement in Zones A and C may occur when a person crosses their legs or when the person rises from a seated position. Also, impingement in Zones A and C may occur when a person is in the sleep position where the person lays on their side and forms a "FIG. 4" with their top leg, i.e., if a person is laying on their left side then the FIG. 4 is formed with their right leg, thus flexing and internally rotating the hip joint. An extreme configuration may depend on the original respective starting positions of constrained portions 14 and femoral component 50.

In an alternative embodiment, Zones A and B could be a single sloped surface and Zones C and D could be a single sloped surface to facilitate similar movements upon impingement by femoral neck 51, as described above.

Although described above with reference to a prosthetic hip joint assembly, the present invention may be used in a similar manner with a prosthetic shoulder joint assembly.

While this invention has been described as having exemplary designs, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A prosthetic joint assembly, comprising:
   a shell;
   a liner rotatably receivable within said shell and defining a longitudinal axis and a hemispherical axis located in a hemispherical plane, said longitudinal axis extending perpendicular to said hemispherical plane, said liner being configured to rotate about said longitudinal axis relative to said shell while being constrained from translating axially along said longitudinal axis relative to said shell, said liner comprising:
   a base portion substantially disposed on a first side of said hemispherical plane; and
   at least one constraining element projecting from said base portion and substantially disposed on a second side of said hemispherical plane, each said constraining element including at least one inclined surface; and
   a prosthesis including a neck and a head, said head receivable within said liner, whereby contact between said neck and said at least one inclined surface induces primarily rotational movement of said liner within said shell about said longitudinal axis.

2. The prosthetic joint assembly of claim 1, wherein said shell comprises an acetabular shell, said prosthesis comprises a femoral prosthesis, said neck comprises a femoral neck, and said head comprises a femoral head.

3. The prosthetic joint assembly of claim 1, wherein said base portion includes an axial movement retention element in engagement with at least a portion of said shell, whereby said axial movement retention element prevents relative axial movement of said liner with respect to said shell along said longitudinal axis.

4. The prosthetic joint assembly of claim 3, wherein said axial movement retention element comprises a radial protrusion formed on an exterior surface of said liner that extends transverse to said longitudinal axis, said protrusion engageable with a groove formed on an interior surface of said shell.

5. The prosthetic joint assembly of claim 4, wherein said protrusion of said liner includes an inclined surface that facilitates insertion of said protrusion into said groove of said shell.

6. The prosthetic joint assembly of claim 3, wherein said axial movement retention element comprises a protrusion that extends from at least one of said liner and said shell.

7. The prosthetic joint assembly of claim 1, wherein each said constraining element includes a plurality of inclined surfaces of different pitch.

8. The prosthetic joint assembly of claim 1, wherein said at least one constraining element forms a snap-fit engagement with said head to axially constrain said head within said liner.

9. An acetabular cup for use with a prosthetic hip joint assembly including a femoral component having a femoral head and a femoral neck, comprising:
   an acetabular shell; and
   a liner rotatably receivable within said acetabular shell and defining a longitudinal axis and a hemispherical axis located in a hemispherical plane, said longitudinal axis extending perpendicular to said hemispherical plane, said liner comprising:
   a base portion substantially disposed on a first side of said hemispherical plane; and
   at least one constraining element projecting from said base portion and substantially disposed on a second side of said hemispherical plane, each said constraining element including at least one inclined surface;
   wherein said liner is primarily rotatable with respect to said shell about said longitudinal axis while being constrained from translating axially along said longitudinal axis with respect to said shell.

10. The acetabular cup of claim 9, wherein said base portion includes an axial movement retention element in engagement with at least a portion of said acetabular shell, whereby said axial movement retention element prevents relative axial movement of said liner with respect to said acetabular shell along said longitudinal axis.

11. The acetabular cup of claim 10, wherein said axial movement retention element comprises a radial protrusion formed on an exterior surface of said liner that extends transverse to said longitudinal axis, said protrusion engageable with a groove formed on an interior surface of said acetabular shell.

12. The acetabular cup of claim 9, wherein each said constraining element includes a plurality of inclined surfaces of different pitch.

13. The acetabular cup of claim 9, wherein said at least one constraining element forms a snap-fit engagement with the femoral head to axially constrain the femoral head within said liner.

14. An acetabular cup for use with a prosthetic hip joint assembly including a femoral component having a femoral head and a femoral neck, comprising:
   an acetabular shell; and
   a liner rotatably receivable within said acetabular shell and defining a longitudinal axis and a hemispherical axis located in a hemispherical plane, and said longitudinal axis extending perpendicular to said hemispherical plane, said liner being configured to rotate about said longitudinal axis relative to said acetabular shell while being constrained from translating axially along said longitudinal axis relative to said acetabular shell, said liner comprising:
   a base portion substantially disposed on a first side of said hemispherical plane; and
   means for constraining the femoral head within said liner, said means for constraining disposed on a second side of said hemispherical plane and including means for inducing primarily rotation of said liner within said acetabular shell about said longitudinal axis upon contact with the femoral neck.

15. The acetabular cup of claim 14, further comprising means for preventing axial translation between said liner and said acetabular shell along said longitudinal axis.

16. The acetabular cup of claim 15, wherein said means for preventing comprises a radial protrusion formed on an exterior surface of said liner that extends transverse to said longitudinal axis and a groove formed on an interior surface of said acetabular shell, said protrusion engaging said groove.

17. The acetabular cup of claim 14, wherein said means for constraining comprises at least one constraining element projecting from said base portion and substantially disposed on a second side of said hemispherical plane.

18. The acetabular cup of claim 14, wherein said means for inducing comprises at least one inclined surface.

19. The acetabular cup of claim 14, wherein said means for inducing comprises a plurality of inclined surfaces of different pitch.

20. The acetabular cup of claim 14, wherein said means for constraining forms a snap-fit engagement with the femoral head.

* * * * *